United States Patent [19]
Björkling et al.

[11] Patent Number: 6,071,960
[45] Date of Patent: Jun. 6, 2000

[54] POLYOL SUCCINATES AND THEIR PHARMACEUTICAL FORMULATION

[75] Inventors: Fredrik Björkling, Helsingborg, Sweden; Willy Jean Malaisse, Brussels, Belgium

[73] Assignee: Leo Pharmaceuticals Products Ltd. A/S (Løvens kemiske Fabrik Produktion-saktieselskab, Ballerup, Denmark

[21] Appl. No.: 09/202,348

[22] PCT Filed: Jun. 4, 1997

[86] PCT No.: PCT/EP97/02966

§ 371 Date: Dec. 14, 1998

§ 102(e) Date: Dec. 14, 1998

[87] PCT Pub. No.: WO97/47584

PCT Pub. Date: Dec. 18, 1997

[30] Foreign Application Priority Data

Jun. 13, 1996 [GB] United Kingdom .................. 9612331

[51] Int. Cl.[7] .......................... C07C 69/40; A61K 31/225
[52] U.S. Cl. ............................................. 514/547; 560/190
[58] Field of Search ................................ 514/547; 560/190

[56] References Cited

U.S. PATENT DOCUMENTS

| | | |
|---|---|---|
| 2,379,251 | 6/1945 | Muskat et al. . |
| 4,325,963 | 4/1982 | Hitzel et al. . |
| 5,512,549 | 4/1996 | Chen et al. . |

FOREIGN PATENT DOCUMENTS 08301814  11/1996  Japan .

OTHER PUBLICATIONS

Fahien, L. A., et al J Biol Chem vol. 263 No. 27 pp 13610–4. See abstract, 1988.
Virkamaki, A. et al J Clin Endocrinol Metab vol. 74 No. 3 pp 673–9. See p. 673, 1992.

*Primary Examiner*—Gary Geist
*Assistant Examiner*—Leigh C. Maier
*Attorney, Agent, or Firm*—Pillsbury, Madison & Sutro LLP

[57] ABSTRACT

Compounds of general formula (I) in which Y and Q are the same or different and are hydrogen atoms or $C_{1-6}$ alkyl groups, optionally substituted by 1–4 hydroxy or 1–4 $R^3O_2CCH_2CH_2CO_2$— groups, where $R^3$ is a hydrogen atom or a $C_{1-6}$ alkyl group which may be straight or branched and saturated or unsaturated, and $R^1$ and $R^2$ are the same or different and are $C_{1-6}$ alkyl groups, which may be straight or branched and saturated or unsaturated, and solvates and prodrugs of these compounds and the salts of compounds in which $R^3$ is a hydrogen atom. These compounds can be used in the treatment of diseases caused by or resulting in metabolic dysfunction and/or energy deprivation, such as diabetes, acute starvation, endotoxemia, sepsis, systemic inflammatory response syndrome and multiple orgen dysfunction syndrome.

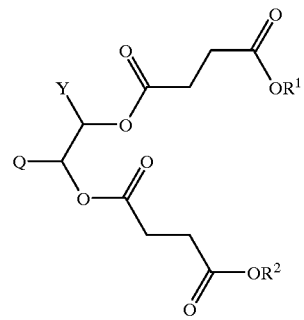

(I)

11 Claims, No Drawings

POLYOL SUCCINATES AND THEIR PHARMACEUTICAL FORMULATION

This invention relates to a hitherto unknown class of compounds which show effect in metabolic diseases including diabetes, acute starvation, endotoxemia, sepsis, systemic inflammatory response syndrome (SIRS) and multiple organ failure, to pharmaceutical preparations containing these compounds, to dosage units of such preparations, and to their use in the treatment and prophylaxis of said diseases and other diseases caused by or resulting in a disturbed metabolism and/or energy deprivation.

The compounds of the present invention are represented by the general formula I

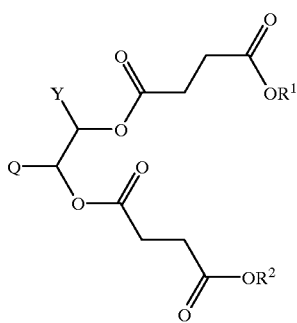

in which
Y and Q are the same or different and are hydrogen atoms or $C_{1-6}$ alkyl groups, optionally substituted by 1–4 hydroxy or 1–4 $R^3O_2CCH_2CH_2CO_2$— groups, where $R^3$ is a hydrogen atom or a $C_{1-6}$ alkyl group which may be straight or branched and saturated or unsaturated, and
$R^1$ and $R^2$ are the same or different and are $C_{1-6}$ alkyl groups, which may be straight or branched and saturated or unsaturated,
and solvates and prodrugs of these compounds and the salts of compounds in which $R^3$ is a hydrogen atom.

Examples of $R^1$ and $R^2$ include, but are not limited to, methyl, ethyl, n-propyl, butyl, allyl and isopropyl.

Examples of Q and Y, include, but-are not limited to, hydrogen, methyl, ethyl, hydroxymethyl, dihydroxyethyl, methyl butandioic acid esters of formula $R^3O_2CCH_2CH_2CO_2CH_2$—, and ethyl dibutandioic acid esters of formula

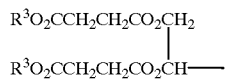

Preferably, Y and Q stand for $C_1$–$C_2$ alkyl, optionally substituted with 1–2 hydroxy or 1–2 $R^3O_2CCH_2CH_2CO_2$— groups, or one of Y and Q is a hydrogen atom and the other is such a group. Particularly important compounds of the invention are 1,2,3,-trihydroxypropane-1,2,3-trimethyl-tributandioate and 1,2,-dihydroxypropane-1,2-dimethyl-dibutandioate.

The compounds of the invention can comprise more than one stereoisomeric form (e.g. R and S configurations at one or more stereochemical centres). The invention covers all these stereoisomers in pure form as well as mixtures thereof. In addition, prodrugs of I in which one or more of the hydroxy groups are masked as groups which can be reconverted to hydroxy groups in vivo are also envisaged.

The compounds of formula I may be obtained in crystalline form either directly by concentration from an organic solvent or by crystallisation or recrystallisation from an organic solvent or mixture of said solvent and a cosolvent which may be organic or inorganic, such as water. The crystals may be isolated in essentially solvent-free form or as a solvate, such as a hydrate. The invention covers all crystalline modifications and forms and also mixtures thereof.

Compounds in which $R^3$ is a hydrogen atom are capable of salt formation with inorganic and organic bases, for example alkali metal, alkaline earth metal and organic amine salts.

It has recently been shown that esters of 1,4-butandioic acid exhibit an insulinotropic activity. The insulinotropic action is believed to be a result of the metabolism of the compound in the S-cell via the Krebs cycle to produce energy in form of adenosine triphosphate (ATP), which in turn causes release of insulin. The direct access of intermediates to the Krebs cycle is of particular importance where the normal glycolytic pathway is dysfunctional as has been indicated in type 2 diabetes. Glucose is a natural trigger for insulin release via its metabolism, however in diabetes its insulinotropic potency is weakened probably due to a metabolic defect early in the metabolic sequence.

A similar metabolic event may also take place in other cell types and any cells deprived of energy (ATP) may benefit from the treatment with particular Krebs cycle intermediates.

Our present findings suggest the beneficial use of the compounds of this invention in the treatment and prophylaxis of diseases characterized by a dysfunction in the metabolism and energy status e.g. diabetes, endotoxemia, severe starvation, sepsis, systemic inflammatory response syndrome (SIRS), and multiple organ dysfunction syndrome (MODS).

The compounds of the present invention differ structurally from the above mentioned esters of 1,4-butandioic acid by being polyols esterified by two or more 1,4-butandioic acid derivatives.

The structurally closest related compounds known are the trisuccinic acid ester of 1,2,3-trihydroxy propane, (K. A., Adrianov; N. I., Tosomaya; L. M., Khananashvili; E. A. Mokhir Plasticheskie Massy 7, 15–16, 1966), and disuccinic acid ester of 1,2-dihydroxyethane (JP 94-28525) which both differ in the degree of esterification of the succinic acid as compared to the compounds of the present invention. The above mentioned compounds have not been used for pharmaceutical purposes, and the structural difference between these and the compounds of the present invention is of profound importance for the biological effect. They show a favourable biological activity, good bioavailability, and low toxicity.

The present compounds are intended for use in pharmaceutical compositions which are useful in the treatment of human and veterinary disorders as described above. The compounds of the present invention were surprisingly found to exhibit potent insulinotropic activity. This measure shows a direct correlation with the energy status of the cells, thus it can be used as a screening tool for the effect of these compounds.

For measurement of insulin release, groups of eight islets each were incubated for 90 min in 1.0 ml bicarbonate-buffered medium containing bovine serum albumin (5.0 mg/ml) and D-glucose (7.0 mM). The insulin released by the islets in the incubation medium was then assayed by radio-immunological back titration procedure (Malaisse-Lage F, Malaisse W J, "Insulin release by pancreatic islets" in Methods in Diabetes Research (Larner J, Pohl S L, eds.) Vol I, part B, John Wiley and Sons, New York, 1984: 147–152).

The amount required of a compound of formula I hereinafter referred to as the active ingredient) for therapeutic effect will, of course, vary both with the particular compound, the route of administration and the mammal under treatment. The compounds of the invention can be administered by the parenteral, intra-articular, enteral or topical routes. They are well absorbed when given enterally and this is the preferred route of administration in the treatment of systemic disorders.

The compounds of the present invention may be prepared by direct esterification of the corresponding polyol or polyol derivative by the desired succinic acid derivative. To obtain compounds of the general formula I, where $R^1 \neq R^2$, selectively protected polyols may be used in the preparation as outlined in scheme I. Y, Q, $R^1$, and $R^2$ are defined as above, and X is a leaving group such as chloride. Examples of hydroxy protecting groups are tetrahydropyranyl, trimethysilyl, butyldimethylsilyl, methoxymethyl, ethoxyethyl, and benzyl.

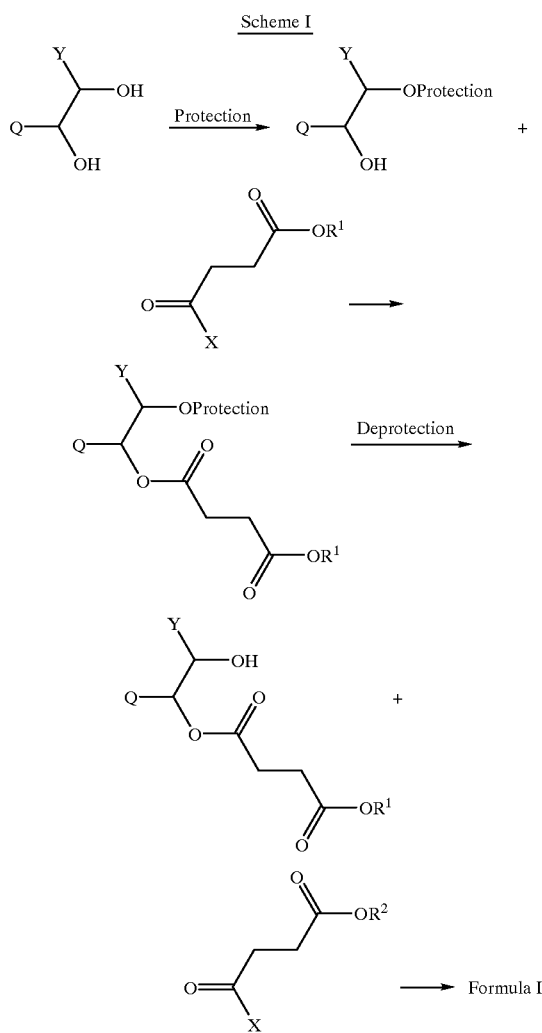

Scheme I

Formula I

Thus, for example, acylation may be effected using an acylating agent such as an acid of formula $R^1O_2CCH_2CH_2COOH$ or a reactive derivative thereof, such as an acid halide (e.g. acid chloride), anhydride or activated ester.

Acylations employing acid halides and anhydrides may if desired be effected in the presence of an acid binding agent such as a tertiary amine (e.g. triethylamine, dimethylaniline or pyridine), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acylations employing acids are desirably conducted in the presence of a condensing agent, for example a carbodiimide such as N,N'-dicyclohexylcarbodiimide or N-ethyl-N'-γ-dimethylaminopropylcarbodimide; a carbonyl compound such as carbonyldiimidazole; or an isoxazolium salt such as N-ethyl-5-phenylisoxozolium perchlorate.

An activated ester may conveniently be formed in situ using, for example, 1-hydroxybenzotriazole in the presence of a condensing agent as set out above. Alternatively, the activated ester may be preformed.

The acylation reaction may be effected in aqueous or non-aqueous reaction media, conveniently at a temperature in the range −20° to +100° C., e.g. −10° to +50° C.

While it is possible for an active ingredient to be administered alone as the raw chemical, it is preferable to present it as a pharmaceutical formulation. Conveniently, the active ingredient comprises from 0.1% to 90% by weight of the formulation.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations, both for human medical and for veterinary use, of the present invention comprise an active ingredient in association with a pharmaceutically acceptable carrier therefore and optionally other therapeutic ingredient (s). The carrier(s) must be "acceptable" in the sense of being compatible with the other ingredients of the formulations and not deleterious to the recipient.

The formulations include e.g. those in a form suitable for oral, rectal, parenteral (including subcutaneous, intramuscular and intravenous), intra-articular and topical administration.

The formulations may conveniently be presented in dosage unit form and may be prepared by any of the methods well known in the art of pharmacy. All methods include the step of bringing the active ingredient into association with the carrier which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. The active ingredient may also be administered in the form of a bolus, electuary or paste.

Formulations for rectal administration may be in the form of a suppository incorporating the active ingredient and a carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for intra-articular administration may be in the form of a sterile aqueous preparation of the active ingredient which may be in microcrystalline form, for example, in the form of an aqueous microcrystal-line suspension, liposomal formulations or biodegradable polymer systems may also be used to present the active ingredient for both intra articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops.

In addition to the aforementioned ingredients, the formulations of this invention may include one or more additional ingredients such as diluents, buffers, flavouring agents, binders, surface active agents, thickeners, lubricants, preservatives, e.g. methyl hydroxybenzoate (including antioxidants), emulsifying agents and the like. The compositions may further contain other therapeutically active compounds usually applied in the treatment of the above mentioned pathological conditions.

The present invention further concerns a method for treating patients suffering from one of the above pathological conditions, said method consisting of administering to a patient in need of treatment an effective amount of one or more compounds of formula I, alone or in combination with one or more other therapeutically active compounds usually applied in the treatment of said pathological conditions. The treatment with the present compounds and/or with further therapeutically active compounds may be simultaneous or with intervals.

In the treatment of systemic disorders typical daily doses range from 0.05 g/kg body weight/day to 5 g/kg bodyweight/day of a compound of formula I are administered. The oral compositions are formulated, preferably as tablets, capsules, or drops, containing from 0.05 g to 1 g, of a compound of formula I, per dosage unit administered one or more times daily. Administration could also be performed by continuous infusion of an amount corresponding to the daily dose.

The invention is further illustrated by the following Preparations and Examples:
General:

For $^1$H nuclear magnetic resonance spectra (300 MHz) chemical shift values ($\delta$) (in ppm) are quoted, unless otherwise specified, for deuteriochloroform solutions relative to internal tetramethylsilane ($\delta$=0.00) or chloroform ($\delta$=7.25). The value for a multiplet, either defined (doublet (d), triplet (t), quartet (q)) or not (m) at the approximate mid point is given unless a range is quoted (s=singlet, b=broad).
General procedure exemplified by

EXAMPLE I 1,2,3,-Trihydroxypropane-1,2,3-trimethyl-tributandioate (Compound 105)

To glycerol (920 mg, 10 mmol) in DMF (30 ml) and pyridine (2.8 ml, 35 mmol), monomethyl succinic acid chloride (4.06 ml, 33 mmol), was slowly added at 0–10° C. After 4 h at 0–10° C., and 16 h at room temp., the mixture was poured into ice-water and extracted with ethyl acetate. The organic phase was washed with HCl (2M), NaHCO$_3$ (aq., sat'd), and NaCl (aq. sat'd). Drying (MgSO$_4$), and evaporation followed by chromatography on silica gel gave 4.1 g (94%) of product. $^1$H NMR $\delta$: 2.65 (m, 12H), 3.69 (s, 9H), 4.20 (dd, 2H), 4.32 (dd, 2H), 5.28 (m, 1H).

EXAMPLE 2

1,2-Dihydroxy ethane-1,2-dimethyl-dibutandioate (Compound 101)

Following the general procedure (Example 1) but replacing glycerol with 1,2-dihydroxy ethane gave the title compound in 71% yield. $^1$H NMR $\delta$: 2.66 (m, 8H), 3.70 (S, 6H), 4.31 (s 4H).

EXAMPLE 3

1,2-Dihydroxy ethane-1,2-diethyl-dibutandioate (Compound 102)

Following the general procedure (Example 1) but replacing glycerol with 1,2-dihydroxy ethane and monomethyl succinic acid chloride with monoethyl succinic acid chloride gave the title compound in 83% yield. $^1$H NMR $\delta$: 1.26 (t, 6H), 2.65 (m, 8H), 4.15 (q, 4H), 4.30 (s, 4H).

EXAMPLE 4

1,2-Dihydroxy propane-1,2-dimethyl-dibutandioate (Compound 103)

Following the general procedure (Example 1) but replacing glycerol with 1,2-dihydroxy propane gave the title compound in 44% yield. $^1$H NMR $\delta$: 1.25 (d, 3H), 2.64 (m, 8H), 3.69 (s, 6H), 4.09 (dd, 1H), 4.20 (dd, 1H), 5.16 (m, 1H).

EXAMPLE 5

1,2-Dihydroxy propane-1,2-diethyl-dibutandioate (Compound 104)

Following the general procedure (Example 1) but replacing glycerol with 1,2-dihydroxy propane and monomethyl succinic acid chloride with monoethyl succinic acid chloride gave the title compound in 58% yield. $^1$H NMR $\delta$: 1.25 (d, 3H), 1.26 (t, 6H), 2.63 (m, 8H), 4.09 (dd, 1H), 4.15 (q, 4H), 4.19 (dd, 1H), 5.16 (m, 1H).

EXAMPLE 6

1,2,3,-Trihydroxypropane-1,2-3-triethyl-tributandioate (Compound 106)

Following the general procedure (Example 1) but replacing monomethyl succinic acid chloride with monoethyl succinic acid chloride gave the title compound in 67% yield. $^1$H NMR $\delta$: 1.26 (t, 9H), 2.64 (m, 12H), 4.15 (q, 6H), 4.20 (dd, 2H), 4.32 (dd, 2H), 5.28 (m, 1h).

EXAMPLE 7

1,2,3,4,-Tetrahydroxybutan-1,2,3,4,-tetramethyl-tetrabutandioate (Compound 107)

Following the general procedure (Example 1) but replacing glycerol with 1,2,3,4,-tetrahydroxy butane gave the title compound in 44% yield. $^1$H NMR $\delta$: 2.64 (m, 16H), 3.69 (s, 12H), 4.22 (m, 2H), 4.36 (m, 2H), 5.29 (m, 2H).

EXAMPLE 8

1,2,3,4-Tetrahydroxybutan-1,2.3.4.-tetraethyl-tetrabutandioate (Compound 108)

Following the general procedure (Example 1) but replacing glycerol with 1,2,3,4,-tetrahydroxy butane and monomethyl succinic acid chloride with monoethyl succinic acid chloride gave the title compound in 44% yield. $^1$H NMR δ: 1.26 (t, 12H), 2.63 (m, 16H), 4.14 (q, 8H), 4.22 (m, 2H), 4.36 (m, 2H), 5.29 (m, 2H).

EXAMPLE 9

1,2,3,4,5-Pentahydroxy-pentane-1,2,3,4,5-pentamethyl-pentabutandioate (Compound 109)

Following the general procedure (Example 1) but replacing glycerol with 1,2,3,4,5-pentahydroxy-pentane gave the title compound.

EXAMPLE 10

1,2,3,4,5-Pentahydroxy-pentane-1,2,3,4,5-pentaethyl-pentabutandioate (Compound 110)

Following the general procedure (Example 1) but replacing glycerol with 1,2,3,4,5-pentahydroxy-pentane and monomethyl succinic acid chloride with monoethyl succinic acid chloride gave the title compound.

EXAMPLE 11

1,2,3,4,5,6-Hexahydroxy-hexane-1,2,3,4,5,6-hexamethyl-hexabutandioate (Compound 111)

Following the general procedure (Example 1) but replacing glycerol with 1,2,3,4,5,6-hexahydroxy-hexane gave the title compound.

EXAMPLE 12

1,2,3,4,5,6-hexahydroxy-hexane-1,2,3,4,5,6-hexaethyl-hexabutandioate (Compound 112)

Following the general procedure (Example 1) but replacing glycerol with 1,2,3,4,5,6-hexahydroxy-hexane and monomethyl succinic acid chloride with monoethyl succinic acid chloride gave the title compound.

EXAMPLE 13

1,2,3,-Trihydroxypropane-1,2-diethyl-dibutandioate-3-butandioic acid (Compound 113)

Step 1. Following the general procedure (Example 1) but replacing glycerol with 1-benzylglycerol and monomethyl succinic acid chloride with monoethyl succinic acid chloride gave the intermediate 1,2,3,-Trihydroxypropane-3-benzyl-1,2-diethyl-di-butandioate.

Step 2. The intermediate benzylether was catalytically hydrogenated (H$_2$) in presence of Pd/C in ethanol which gave 1,2,3,-Trihydroxypropane-1,2-diethyl-dibutandioate.

Step 3. 1,2,3,-Trihydroxypropane-1,2-diethyl-dibutandioate was then further reacted with butanedioic acid anhydride yielding the title compound 113.

EXAMPLE 14

Capsules containing Compound 105

Compound 105 was dissolved in fractionated coconut oil to a final concentration of 10 mg/ml oil. Ten parts by weight of gelatine, 5 parts by weight of glycerin, 0.08 parts by weight potassium sorbate, and 14 parts by weight distilled water were mixed together with heating and formed into soft gelatine capsules. These were then filled each with 100 μl of the oily solution of Compound 105.

EXAMPLE 15

| Tablet containing Compound 105 | |
|---|---|
| Compound 105 (active substance) | 100 mg |
| Lactose | 75 mg |
| Starch | 12 mg |
| Methyl cellulose | 2 mg |
| Sodium carboxymethyl cellulose (CMC—Na) | 10 mg |
| Magnesium stearate | 1 mg |

The active substance, lactose and starch are mixed to a homogeneous state in a suitable mixer and moistened with a 5 percent aqueous solution of methylcellulose 15 cps. The mixing is continued until granules are formed. If necessary, the wet granulation is passed through a suitable screen and dried to a water content of less than 1% in a suitable dryer, e.g. fluid bed or drying oven. The dried granules are passed through a 1 mm screen and mixed to a homogeneous state with CMC-Na. Magnesium stearate is added, and the mixing is continued for a short period of time.

Tablets with a weight of 200 mg are produced from the granulation by means of a suitable tabletting machine.

EXAMPLE 16

| Formulation for injection containing Compound 105 | |
|---|---|
| Compound 105 (active substance) | 1% |
| Sodium chloride | q.s. |
| Ethanol | 10% |
| Water for injection to make | 100% |

The active substance is dissolved ethanol (10%) then water for injection made isotonic with sodium chloride to make 100%. The solution is filled into ampoules and sterilized.

What is claimed is:

1. A compound of formula I

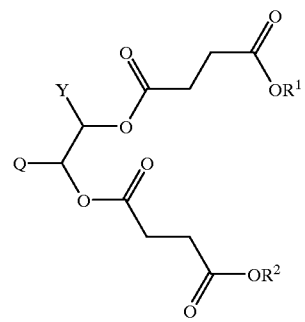

in which
Y and Q are the same or different and are hydrogen atoms or C$_{1-6}$ alkyl groups, optionally substituted by 1–4 hydroxy or 1–4 R$^3$O$_2$CCH$_2$CH$_2$CO$_2$— groups, where R$^3$ is a hydrogen atom or a C$_{1-6}$ alkyl group which may be straight or branched and saturated or unsaturated, and R$^1$ and R$^2$ are the same or different and are straight or branched saturated C$_{1-6}$ alkyl groups, and solvates and prodrugs of these compounds and the salts of compounds in which R$^3$ is a hydrogen atom.

2. A compound according to claim 1 in which R$^1$ and R$^2$ are methyl or ethyl groups.

3. A compound according to claim 1 or claim 2 in which Y and Q are hydrogen atoms or methyl, ethyl, hydroxymethyl or dihydroxyethyl groups or groups of the formula

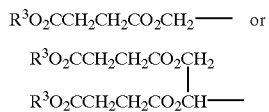

4. A compound according to claim 1 or claim 2 in which y and Q are both methyl or ethyl groups optionally substituted by 1 or 2 hydroxy or 1 or 2 $R^3O_2CCH_2CH_2CO_2$—groups, or one of Y and Q is a hydrogen atom and the other is such a group.

5. A compound according to claim 1, said compound being:
- 1,2,-dihydroxyethane-1,2-dimethyl-dibutandioate;
- 1,2,-dihydroxyethane-1,2-diethyl-dibutandioate;
- 1,2,-dihydroxypropane-1,2-diethyl-dibutandioate;
- 1,2,3,-trihydroxypropane-1,2,3-triethyl-tri-butandioate;
- 1,2,3,4,-tetrahydroxybutan-1,2,3,4,-tetra-methyl-tetrabutandioate; or
- 1,2,3,4,-tetrahydroxybutan-1,2,3,4,-tetra-ethyl-tetrabutandioate.

6. A compound according to claim 1, said compound being:
- 1,2,3,-trihydroxypropane-1,2,3-trimethyl-tri-butandioate.

7. A compound according to claim 1, said compound being:
- 1,2,-dihydroxypropane-1,2-dimethyl-dibutandioate.

8. A pharmaceutical composition comprising a compound according to claim 1 together with one or more pharmaceutically acceptable carriers.

9. A method for obtaining increased insulinotropic activity in a patient in need of such increased activity, which comprises administering to said patient an effective amount of one or more compounds according to claim 1.

10. A process for the preparation of a compound according to claim 1 in which a corresponding polyol is esterified to introduce the desired succinate groups, using selective hydroxy protection in the preparation of compounds in which $R^1$ and $R^2$ are different.

11. A method according to claim 9 for the treatment of diabetes.

* * * * *